United States Patent [19]

Spears

[11] Patent Number: 5,500,341

[45] Date of Patent: Mar. 19, 1996

[54] **SPECIES-SPECIFIC DETECTION OF *MYCOBACTERIUM KANSASII***

[75] Inventor: Patricia A. Spears, Raleigh, N.C.

[73] Assignee: Becton, Dickinson and Company, Franklin Lakes, N.J.

[21] Appl. No.: 308,892

[22] Filed: Sep. 19, 1994

[51] Int. Cl.⁶ .............................. C12Q 1/68; C12P 19/34; C07H 21/04
[52] U.S. Cl. .......................... 435/6; 435/91.2; 536/24.32; 536/24.33; 935/8; 935/17; 935/77; 935/78
[58] Field of Search ................... 435/6, 91.2; 536/24.32, 536/24.33, 24.1, 24.2; 935/16, 17, 77, 78, 8

[56] References Cited

PUBLICATIONS

Yang et al, J. Clin Microbiol (1993) 31:2769–2722.
T. Rogall et al Differentiation of Mycobacterium Species by Direct Sequencing of Amplified DNA J. of General Microbiology (1990) 136, 1915–20.
B. Boddinghaus et al Detection and Identification of Mycobacteria by Amplification of rRNA J. of Clinical Microbiology (Aug. 1990) 1751–59.
B. Ross et al Identification of a Genetically Distinct Subspecies of *Mycobacterium kansasii* J. of Clinical Microbiology (Nov. 1992) 2930–33.
M. Yang et al Isolation of a DNA Probe for Identification of *Mycobacterium kansasii* Including the Genetic Subgroup J. of Clinical Microbiology (Oct. 1993) 2769–72.
Z. Huang et al Identification of *Mycobacterium kansasii* by DNA Hybridization J. of Clinical Microbiology (Oct. 1991) 2125–29.

Primary Examiner—W. Gary Jones
Assistant Examiner—Carla Myers
Attorney, Agent, or Firm—Donna R. Fugit

[57] ABSTRACT

*M. kansasii*-specific oligonucleotide amplification primers and methods for detecting and identifying *M. kansasii* nucleic acids using the amplification primers. One hundred percent of the clinical and environmental *M. kanasii* isolates tested were positive in amplification assays using the inventive amplification primers, with no cross-reactivity in other species of mycobacteria or closely related non-mycobacteria.

19 Claims, 3 Drawing Sheets

FIG-2

```
       51                                      85   86
p6123  ACCAGCGGATC GTCACGGTGC TGCGGG CCAGACGACA   GTACGGCCGG CCAACAGCGC GACGCTGGGA
1201               C                       G                    G         C    G
P6232        G                  T          C                    G         C    G
13638        G                  T          C                 GT G         C    G
724          G                                                  G         C    G
             |———— B1'1 SEQ ID#9 ————|            |———— B1 SEQ ID#8 ————|

190
p6123  TATCCGTCGA ACAGCACCTC GGCGAACTCG ACGGC CTCGGGCGCC CACCAGGAAT CGCCGTCGCA GAACGCGACA
1201     C                                C                    T                T
P6232    CG                    A          C         T          T                T
13638    CG                               C         T                           T
724      CG                                                                     T
         |— S1'1 —|                       |—— D1 SEQ ID#12 ——|
         |—— S1 SEQ ID#4 ——|                        |———— S2 SEQ ID#6 ————|
                |—— SEQ ID#5 ——|                              |—— S2'1 SEQ ID#7 —|

220
p6123  AACGGTGTGT CGCAATGTGC CACACCGACG
1201       C         G A        T
P6232      C         TAC        T
13638   A  C         TAC        TA
724        T                    T
                                |— B2 SEQ ID#10 —|
                                |— B2'1 SEQ ID#11 —|
```

SPECIES-SPECIFIC DETECTION OF *MYCOBACTERIUM KANSASII*

FIELD OF THE INVENTION

The present invention relates to amplification primers and methods for amplifying nucleic acid target sequences. In particular, the invention relates to species-specific amplification of *Mycobacterium kansasii* target sequences.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bows, M. bovis*-BCG, *M. chelonae, M. fortuitum, M. gordonae, M. intracellulare, M. kansasii, M. microti, M. scrofidaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. However, infections caused by Mycobacteria other than tuberculosis (MOTT) have also been increasing. Many of these new cases are related to the AIDS epidemic, which provides an immune compromised population which is particularly susceptible to infection by Mycobacteria. *Mycobacterium avium, Mycobactenum kansasii* and other non-tuberculosis mycobacteria have been found as opportunistic pathogens in HIV-infected and other immune compromised patients. There is an increasing need for rapid diagnosis of these infections, as they can disseminate rapidly and may be fatal within a short period of time.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC system (Becton Dickinson Microbiology Systems, Sparks, Md.) can decrease the time for diagnosis to one to two weeks. However, there is still a need to reduce the time required for diagnosing mycobacterial infections to less than a week, preferably to about one day. Oligonucleotide probe based assays such as Southern hybridizations or dot blots are capable of returning a rapid result (i.e., in one day or less). Genus- and species-specific primers may also be used in direct assays of clinical samples by nucleic acid amplification. However, both of these rapid detection and identification methods require oligonucleotide probes or primers which are specific for the genus Mycobacteria (tuberculosis and non-tuberculosis) or specific for a particular mycobacterial species if specific identification of the organism is desired.

Conventional laboratory identification of *Mycobacterium kansasii* relies upon biochemical testing and determination of growth characteristics. These include catalase production, urease activity, TWEEN hydrolysis, nitrate reduction and the ability of the bacterium to produce pigment when exposed to light (photochromogenicity). Because several other mycobacterial species exhibit a similar biochemical profile, photochromogenicity is customarily relied upon as the conclusive characteristic for identification of *Mycobacterium kansasii*. However, determination of photochromogenicity requires a pure culture of the organism and this phenotype can be variable, subjective and difficult to determine reliably. For these reasons, there have been attempts to identify *Mycobacterium kansasii* by species-specific hybridization or nucleic acid amplification using oligonucleotide probes. Z. H. Huang, et al. (1991. J. Clin. Microbiol. 29, 2125–2129) have reported a DNA probe obtained from a genomic library with a degree of species-specificity for *Mycobacterium kansasii*. This clone (pMK1-9) showed some cross-hybridization with other species, including *M. gastri*, and did not detect a genetically distinct subgroup of *M. kansasii*. The nucleotide sequence of pMK1-9 was not reported, nor was the gene from which it may have been derived identified. B. C. Ross, et al. (1992. J. Clin. Microbid. 30, 2930–2933) also reported identification of genetically distinct subspecies of *M. kansasii* using the pMK1-9 probe, a 65kDa antigen gene probe and a commercial DNA probe test employing probes which specifically hybridize to rRNA (ACCU-PROBE, Gen-Probe, San Diego, Ca.). Amplification primers which hybridize to the 16S rRNA gene were used to sequence and compare the 16S rRNA gene sequences of the *M. kansasii* variants studied. M. Yang, et al. (1993. J. Clin. Microbid. 31, 2769–2772) have reported isolation of a sequence from a clinical isolate which, when used as a hybridization probe, exhibits *M. kansasii* species-specificity. This probe (p6123) hybridized to all *M. kansasii* strains tested, including the subgroup which is pMK1-9 negative.

T. Rogall, et al. (1990. J. Gen. Microbiol. 136, 1915–1920) used the 16S rRNA sequence in a polymerase chain reaction (PCR) based sequencing strategy for identification of mycobacterial species. However, these primers could not be used to differentiate *M. gastri* from *M. kansasii* because the 16S rRNA sequence from these two species is identical in spite of their differing phenotypic characteristics. Similar studies have been published by B. Böddinghaus, et al. (1990. J. Clin. Microbiol. 28, 1751–1759), who reported oligonucleotides derived from 16S rRNA sequences which are specific for the *M. tuberculosis* group, i.e., *M. avium-M. paratuberculosis*, and *M. intracellulare*.

The present invention provides nucleic acid sequences useful as amplification primers for species-specific detection and identification of *Mycobacterium kansasii*. Species-specificity means that the inventive primers amplify a target sequence in *M. kansasii* nucleic acids with little or no detectable amplification of target sequences of other species of mycobacteria or of closely related microorganisms such as *M. gastri, Rhodococcus rhodochrous* and *Nocardia asteroides*. The amplification primers of the invention are derived from the p6123 sequence previously reported by Yang, et al. (1993), however, these authors had previously used only the full-length p6123 sequence to demonstrate species-specificity by probe hybridization (e.g., Southern blots). It was not known prior to the present invention whether short amplification primers could be designed which would retain species-specificity and also function as primers for SDA.

The primers may be used after culturing a sample as a means for confirming identity of the culture. Alternatively, they may be used prior to culturing for detection and identification of mycobacterial DNA using nucleic acid amplification techniques as is known in the art. In either case, the inventive primers and diagnostic methods provide a means for rapidly discriminating between *M. kansasii* and other species of mycobacteria, allowing the practitioner to rapidly identify this microorganism without resorting to the time-consuming phenotypic and biochemical procedures customarily relied upon. Such rapid identification of the specific etiological agent involved in a mycobacterial infection provides information which can be used to determine appropriate therapy within a short period of time.

SUMMARY OF THE INVENTION

The present invention provides oligonucleotide amplification primers which exhibit *M. kansasii*-specificity in nucleic acid amplification reactions. Also provided are methods for detecting and identifying *M. kansasii* nucleic acids using the amplification primers of the invention. One hundred percent of the clinical and environmental *M. kanasii* isolates tested were positive in amplification assays using the inventive amplification primers.

DESCRIPTION OF THE DRAWINGS

FIG. 2 is an illustration of the nucleotide sequences corresponding to nucleotides 51-220 of p6123 (SEQ ID NO:16) in five strains of *M. kansasii*, showing the sites of hybridization of the amplification primers.

DETAILED DESCRIPTION OF THE INVENTION

Figure 1A:
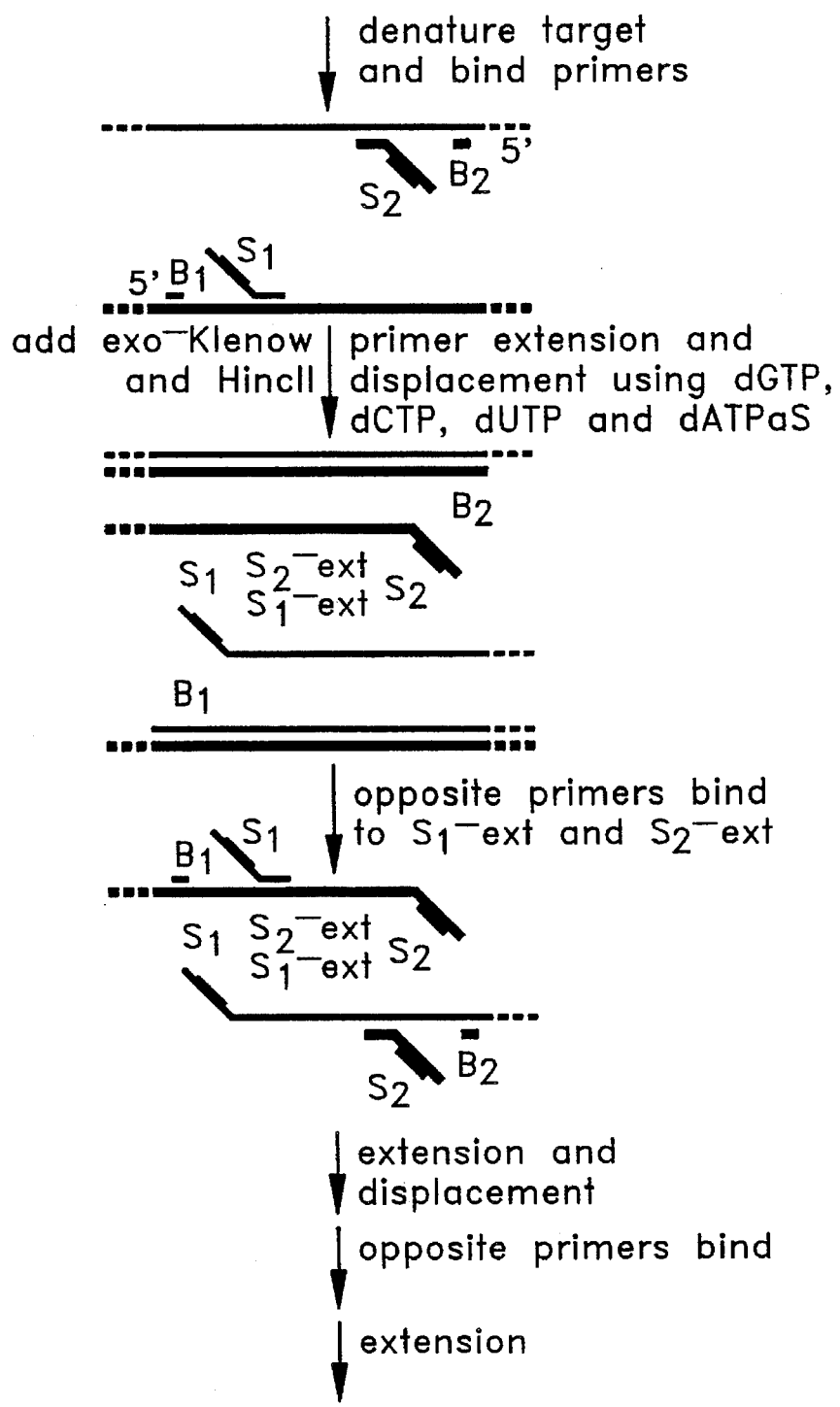
FIG. 1A and 1B illustrate the target generation scheme for Strand Displacement Amplification (SDA - left side) and the reaction steps for exponential amplification of a target sequence by SDA (right side).
Figure 1B:
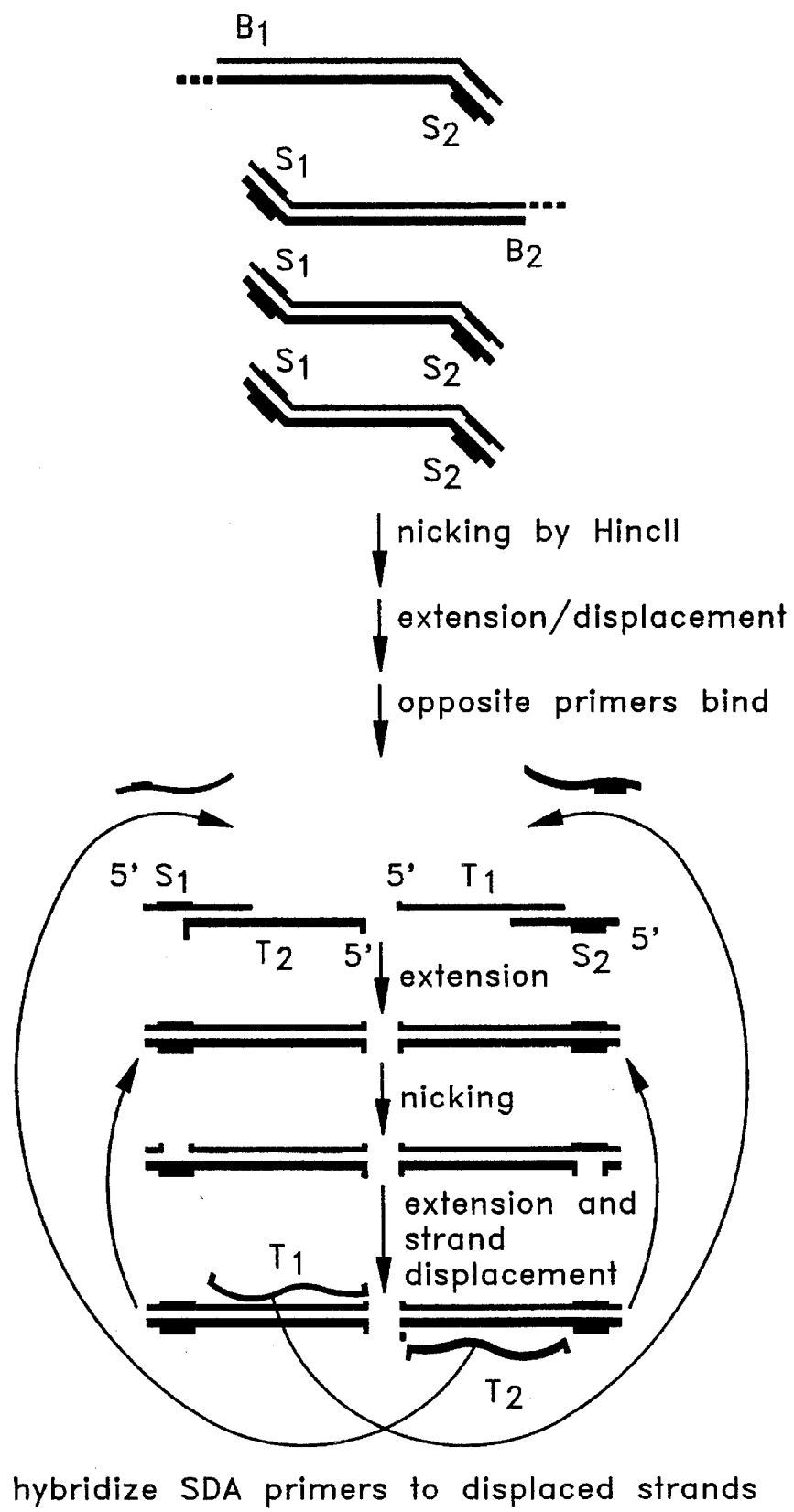

Oligonucleotides according to the invention are particularly useful as amplification primers for detecting *M. kansasii* target nucleic acid sequences in a sample suspected of containing mycobacteria. The samples may comprise isolated nucleic acids, isolated microorganisms, or they may be clinical samples. Typically, clinical samples are in the form of a biological fluid or tissue, e.g., sputum, bronchial washings, gastric washings, blood, milk, lymph, skin and soft tissues. Prior to hybridization with the primers of the invention, samples suspected of containing intact microorganisms rather than free nucleic acids are generally treated using methods known in the art to release nucleic acids from any microorganisms which may be present. In addition, sputum samples are typically liquified prior to releasing nucleic acids for analysis. Appropriate liquification methods are known in the art. As mycobacteria infect both human and non-human animal species, the present invention is applicable to both human and veterinary diagnostic procedures and the sample may be obtained from either source. As humans are susceptible to infection from a variety of Mycobacteria, including *M. tuberculosis, M. kansasii, M. avium, M. intracellulare, M. scrofulaceum* and *M. fortuitum*, the instant primers and diagnostic methods may be used to rapidly identify cases in which *M. kansasii* is the etiologic agent, thereby aiding in selection of an appropriate therapy.

The oligonucleotide primers of the invention are preferably used to detect and/or identify *Mycobacterium kansasii* by amplification of mycobacterial nucleic acid target sequences. However, the portion of the primer which hybridizes to the target sequence may also be used as a hybridization probe for direct detection of target *M. kansasii* nucleic acid in various nucleic acid hybridization methods. Hybridization methods include Southern blots for detection of DNA, Northern blots for detection of RNA and dot blots for detection of either DNA or RNA. They are generally well-known in the art and are described in *Molecular Cloning: A Laboratory Manual,* 2nd ed., J. Sambrook, E. F. Fritsch and T. Maniatis, Cold Spring Harbor Laboratory Press, 1989. In the preferred embodiment, the presence of *M. kansasii* in a sample is detected and/or identified by species-specific amplification of target nucleic acid sequences. In this embodiment, the amplification primers of the invention are used in conventional nucleic acid amplification protocols. Any amplification protocol which relies on cyclic, specific hybridization of primers to the target nucleic acid may be used, e.g., Polymerase Chain Reaction (PCR: U.S. Pat. Nos. 4,683,195; 4,683,202; 4,800,159; 4,965,188), Strand Displacement Amplification (SDA) (G. Walker, et al. 1992. *Proc. Nat. Acad. Sci. USA* 89,392–396; G. Walker, et al. 1992. *Nucl. Acids Res.* 20,1691–1696; U.S. Pat. No. 5,270, 184 which is hereby incorporated by reference), nucleic acid based sequence amplification (NASBA: U.S. Pat. No. 5,130,238 to Cangene), transcription based amplification (D. Kwoh, et al. 1989. *Proc. Nat. Acad. Sci. USA* 86,1173–1177), self-sustained sequence replication (J. Guatelli, et al. 1990. *Proc. Nat. Acad Sci. USA* 87,: 1874–1878) or the Qβ replicase system (P. Lizardi, et al. 1988. *BioTechnology* 6,1197–1202). The preferred amplification methods for use with the primers of the invention are methods which utilize cyclic, specific hybridization of primers to the target sequence, extension of the primers using the target sequence as a template and displacement of the extended primers from the target sequence, e.g., PCR and SDA.

An amplification primer is a primer for amplification of a target sequence by primer extension or ligation of adjacent primers hybridized to the target sequence. For amplification by SDA, the oligonucleotide primers are preferably selected such that the GC content is low, preferably less than 70% of the total nucleotide composition of the probe. Similarly, for SDA the target sequence preferably has a low GC content to minimize secondary structure. The 3' end of an SDA amplification primer (the target binding sequence) hybridizes at the 3' end of the target sequence. The target binding sequence confers target specificity on the amplification primer. The SDA amplification primer further comprises a recognition site for a restriction endonuclease near its 5' end. The recognition site is for a restriction endonuclease which will nick one strand of a DNA duplex when the recognition site is hemimodified, as described by Walker, et al. (1992. *PNAS* 89, 392–396). For the majority of the SDA reaction, the amplification primer is responsible for exponential amplification of the target sequence. The SDA amplification primer may also be referred to as the "S" primer, e.g., $S_1$ and $S_2$ when a pair of amplification primers is used for amplification of a double stranded sequence. For other amplification methods which do not require attachment of specialized sequences to the ends of the target, the amplification primer generally consists of only the target binding sequence. For example, *M. kansasii*-specific amplification by PCR according to the invention will employ amplification primers consisting of the target binding sequences of the SDA primers. These are hybridized to the target sequence, extended by polymerase and the extension products are displaced by heating as is customary for PCR.

A bumper or external primer is a primer used in SDA which anneals to a target sequence upstream of the amplification primer such that extension of the bumper primer displaces the downstream amplification primer and its extension product. Bumper primers may also be referred to as "B" primers, e.g., $B_1$ and $B_2$ when a pair of bumper primers is used to displace the extension products of a pair of amplification primers. Extension of bumper primers is one method for displacing the extension products of amplification primers, but heating is also suitable.

The terms target or target sequence refer to nucleic acid sequences to be amplified by amplification primers. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they also contain copies of the original target sequences to which the amplification primers hybridize.

Copies of the target sequence which are generated during the amplification reaction are referred to as amplification products, amplimers or amplicons.

The term extension product refers to the single-stranded copy of a target sequence produced by hybridization of an amplification primer and extension of the amplification primer by polymerase using the target sequence as a template.

The preferred method for amplification of the *M. kansasii* target sequence is Strand Displacement Amplification (SDA). The SDA target generation and amplification reaction schemes are illustrated in FIG. 1. The target DNA is heat denatured in the presence of an excess of four primers ($B_1$, $B_2$, $S_1$ and $S_2$). $S_1$ and $S_2$ are amplification primers containing target binding sequences at their 3' ends and a recognition site for a restriction endonuclease (e.g., HincII - $^{5'}$GTTGAC) 5' to the target binding sequences. The restriction endonuclease recognition sites are designated by the raised boxes. For convenience, the following description will use HincII and exo$^-$ Klenow polymerase as examples, however, any of the restriction endonucleases and 3'–5' exonuclease deficient polymerases known for use in SDA may be substituted.

$S_1$ and $S_2$ hybridize to opposite strands of the double stranded target sequence, flanking the region to be amplified. $B_1$ and $B_2$ are external or bumper primers which consist only of target binding sequences and hybridize at positions 5' to $S_1$ and $S_2$. After annealing of the primers to the target at about 40° C., HincII is added along with an exonuclease deficient form of the Klenow fragment of *E. coli* DNA polymerase I (exo$^-$ Klenow). At this point the remaining target generation steps on the left side of FIG. 1 proceed as a single cascade. Exo$^-$ Klenow, which is present in large molar excess over the number of target sequences, simultaneously extends all four primers using dGTP, dCTP, dUTP (or TTP) and dATPαS (deoxyadenosine 5'-[α-thio]triphosphate). $S_1$ and $S_2$ are extended and their extension products are displaced by extension of $B_1$ and $B_2$. The displaced extension products of $S_1$ and $S_2$ ($S_1$-ext and $S_2$-ext) serve as targets for binding of the opposite amplification primers. Further rounds of extension and displacement produce two target fragments with a hemiphosphorothioate HincII site at each end and two longer target fragments with a hemiphosphorothioate HincII site at only one end (bottom left side of FIG. 1). Incorporation of dATPαS in place of dATP in one of the two strands by the polymerase causes the restriction endonuclease to nick one strand rather than cleave both strands of the duplex. "Nicking" refers to the cleavage of one strand of double-stranded DNA as opposed to double-stranded cleavage. HincII nicks the unmodified primer strands of the hemiphosphorothioate recognition sites, leaving intact the modified complementary strands. Exo$^-$Klenow then extends from the 3'-end of the nick and displaces the downstream newly synthesized strand. New $S_1$ and $S_2$ primers bind to the displaced strands and are extended. This is followed by additional nicking and strand displacement steps until the four duplexes at the bottom left side of FIG. 1 converge into the "steady-state" amplification cycle illustrated on the fight side of FIG. 1. During each SDA cycle, the 3' end of $S_1$ hybridizes to the 3'-end of the displaced target strand $T_2$, forming a duplex with 5'-overhangs. Likewise, $S_2$ binds to displaced $T_1$. Exo$^-$Klenow extends the recessed 3'-ends of the duplexes producing hemiphosphorothioate recognition sites which are nicked by HincII. These nicking and extension/displacement steps cycle continuously (short curved arrows on the right side of FIG. 1) because extension at a nick regenerates a nickable HincII recognition site. The strand displaced from the $S_1$-$T_2$ duplex is identical to $T_1$. Likewise, the displaced strand from the $S_2$-$T_1$ duplex is identical to $T_2$. Consequently, target amplification is exponential because each displaced $T_2$ binds a new $S_1$ primer and each displaced $T_1$ binds a new $S_2$ (long curved arrows on the fight side of FIG. 1). Sense and antisense strands are differentiated by thin and thick lines. Intact and nicked HincII recognition sites are represented by ⊥ and ⌋⌊. The partial HincII recognition sites (5'-GAC and its complement 5'-GTC) are present at the 5'-and 3'-ends of displaced strands and are represented by ⌊ and ⌋, respectively.

Little is known about the parameters for design of amplification primers for SDA. In general, target sequences with relatively low GC content and less sequence variability are desirable. However, there must also be two such regions (one for hybridization of each amplification primer) close enough together to be amplified by SDA. SDA in its current form requires shorter targets than does PCR, usually less than about 100 nucleotides. However, even if these criteria can be met, utility of amplification and bumper primers designed in SDA is unpredictable. An amplification primer designed as an exact match to the target sequence for unknown reasons may fail to amplify it, whereas those derived from the same region of the target sequence but containing mismatches may efficiently amplify all variant strains. This may be due in part to undefined effects of the other sequences which comprise the amplification primer (e.g., the restriction endonuclease recognition site and flanking sequences which allow space for the endonuclease to bind). In addition the bumper primers often have a significant influence on amplification even though they are not directed to the target sequence and do not participate directly in the amplification process. It has also been found that the combination of amplification primers and bumper primers can be critical. That is, a bumper primer/amplification primer combination may allow efficient amplification, but when the same bumper primer is used in combination with a different but closely related amplification primer, amplification may be inhibited. Therefore, identification of sequences with little or no variability among Mycobacteria species is a first step but is not sufficient to ensure that amplification primers suitable for use in SDA can be designed. At the present time the process of designing SDA primers relies very much on identifying two apparently promising areas of target sequence (low GC content, less sequence variability, proximity to each other), designing a series of related or overlapping primers, and testing different combinations of primers in SDA to determine which, if any, support amplification.

As nucleic acids do not require complete complementarity in order to hybridize, it is to be understood that the probe and primer sequences herein disclosed may be modified to some extent without loss of utility as *M. kansasii*-specific probes and primers. As is known in the art, hybridization of complementary and partially complementary nucleic acid sequences can be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain *M. kansasii*-specificity require only routine experimentation and are well within the ordinary skill in the art.

The amplification products generated using the inventive primers may be detected by a characteristic size, for example on polyacrylamide or agarose gels stained with ethidium bromide. Alternatively, *M. kansasii* nucleic acid in a sample or specifically amplified *M. kansasii* target sequences may be detected by hybridization to the inventive amplification primers or their target binding sequences. For detection by hybridization the oligonucleotides are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

For detection of amplified target sequences, the primers used in the amplification reaction may be tagged and used as detector probes because the primers are incorporated into the amplification product. Alternatively, at least one tagged probe different from the amplification primers may be used as a probe for detection of amplified target sequences by hybridization. This probe should be selected to hybridize to a sequence in the target which is between the amplification primers, i.e., an internal probe. Alternatively, either the primer or the internal probe may be tagged and extended by polymerase for detection of amplification products as described by Walker, et al., *Nucl. Acids Res., supra.*

For convenience, amplification primers for species-specific detection and identification of *M. kansasii* may be packaged in the form of a kit which may further include other components and reagents for performing the detection methods. By way of example, such a kit contains at least one pair of amplification primers according to the present invention. For detection by hybridization, a hybridization solution such as 6X SSC (0.9M sodium chloride, 0.09M sodium citrate, pH 7.0), 0.1M EDTA pH 8.0, 5X Denhardt's solution (0.1% w/v FICOLL TYPE 400, 0.1% w/v polyvinylpyrrolidone, 0.1% w/v bovine serum albumin) and 100 µg/ml sheared denatured salmon sperm DNA, or other reagents known to be useful for probe hybridization may also be included. See *Molecular Cloning: A Laboratory Manual,* supra. Alternatively, reagents appropriate for use with one of the known nucleic acid amplification methods may be included with *M. kansasii*-specific amplification primers. The components of the kit are packaged together in a common container, typically including instructions for performing a specific embodiment of the inventive methods. Additional, optional components may also be included in the kit, e.g., a second probe tagged with a label suitable for use as a detection probe, and reagents or means for performing detection of the label.

Because target sequence heterogeneity among isolates of a species may prevent the design of species-specific amplification primers and preclude species-specific amplification of the target, it was first necessary to determine the extent of heterogeneity of the p6123 sequence among strains of *M. kansasii*. p6123 had previously exhibited species-specificity only as a hybridization probe. Hybridization detection, such as on Southern blots, allows a high level of sequence mismatching (as much as 70%) which is not tolerable for amplification primers. By aligning the p6123 sequence with an analogous but variant sequence derived from a different strain of *M. kansasii* (p6232), PCR primers were designed to amplify a subfragment of the analogous sequence in three additional isolates of *M. kansasii* (TMC1201, LCDC724 and 13638). SEQ ID NO: I (MY-1) is an antisense primer corresponding to nucleotides 503–484 of the p6123 sequence. Two sense primers were synthesized corresponding to nucleotides 50–69. The first, SEQ ID NO:2 (MY2a) has an adenine at position 58 whereas the second, SEQ ID NO:3 (MY-2g) has a guanine at position 58. SEQ ID NO: 1, SEQ ID NO:2 and SEQ ID NO:3 were all synthesized on an Applied Biosystems 380B Synthesizer as recommended by the manufacturer. The oligonucleotides were deprotected using ammonium hydroxide at 50° C. for 16 hours, then OPC purified as recommended by the manufacturer (Applied Biosystems).

PCR amplifications were performed in 100 µl reactions consisting of 10 mM Tris-HCl pH 8.3, 50 mM KCl, 1.5 mM MgCl$_2$, 0.001% (w/v) gelatin, 200 µM dATP, 200 µM dCTP, 200 µM dGTP, 200 µM TTP, 1.0 µM of each primer (sense and antisense) and $10^6$ to $10^4$ molecules of target DNA. The reactions were overlaid with mineral oil and heated to 95° C. for 5 minutes. AMPLITAQ polymerase (Perkin Elmer Cetus) was added to each reaction (2.5 Units/100 µl) and the thermocycling was started. The thermocycling protocol, for a total of 30 cycles, was as follows: 94° C. for 1 minute 30 seconds, 55° C. for 2 minutes, 72° C. for 3 minutes. This was followed by a 7 minute incubation at 72° C. The samples were then stored at 4° C.

A 454 base pair product was amplified from *M. kansasii* TMC 1201, LCDC 724 and 13638 using SEQ ID NO:1 and SEQ ID NO:2. A 454 base pair product was also amplified from LCDC 724 and 13638, but not from TMC 1201, using SEQ ID NO:1 and SEQ ID NO:3. The amplification products were subcloned into pUC18 plasmids digested with SmaI (Pharmacia LKB) and two independent clones from each strain were sequenced using an Applied Biosystems 373A sequencer and Prism Dye terminator cycle sequencing kits (Applied Biosystems) as recommended by the manufacturer. A substantial amount of sequence variation was found among the strains. The sequence amplified from *M. kansasii* 13638 (SEQ ID NO:15) was identical to the sequence of p6232 but differed from p6123. The sequence from TMC1201 (SEQ ID NO:13) and LCDC724 (SEQ ID NO:14) differed from both p6123 and p6232. By aligning the sequences of the various *M. kansasii* isolates (p6123, p6232, TMC 1201, LCDC724 and 13638 - FIG. 2), several amplification and bumper primers were designed which could potentially amplify all five isolates. These were selected based on GC content of the target sequence, proximity of the binding sites of the two amplification primers and sequence variability.

Strand Displacement Amplification (SDA) reactions were generally performed as previously described (Walker et al., *Nucl. Acids Res., supra*), with substitution of dUTP for TTP to allow for inactivation (decontamination) of amplicons generated using uracil DNA glycosylase (UDG). The reactions were performed in a 50 µl volume consisting of 6 mM MgCl$_2$, 0.2 mM each dGTP, dCTP and α-thio-dATP (2'-deoxyadenosine 5'-O-(1-thiotriphosphate), 0.5 mM dUTP, 100 µg/ml acetylated bovine serum albumin, 1 ng/µl human placental DNA, 42.5 mM K$_i$PO$_4$pH 7.6, 0.5 µM primers S$_1$ and S$_2$, 0.05 µM primers B$_1$ and B$_2$, 3 units/µl HincII, 0.1 unit/µl exo⁻Klenow DNA polymerase (United States Biochemical) and varying amounts of target DNA. The reactions also contained 15% (v/v) dimethylsulfoxide (DMSO). Prior to the addition of HincII, exo⁻Klenow and MgCl$_2$, the reactions were heated at 95° C. for 2 minutes to denature the target DNA, followed by 2 minutes at 41° C. to anneal the primers. Following addition of the enzymes and MgCl$_2$, the reactions were incubated at 41° C. for 2 hours for amplification. Amplification was terminated by heating for 2 minutes at 95° C. Amplification products were detected by hybridization and extension of a $^{32}$P-labeled primer (SEQ ID NO:12) followed by denaturing polyacrylamide gel electrophoresis as described previously (Walker et al., *Nucl. Acids Res.*, supra).

SEQ ID NO:4 and SEQ ID NO:5 (MYs1 and MYs1.1) were designed as S$_1$ amplification primers for SDA. SEQ ID NO:6 and SEQ ID NO:7 (MYs2 and MYs2.1) were designed as S$_2$ amplification primers for SDA. They comprise a target binding region which hybridizes to the target sequence and a recognition site for the restriction endonuclease HincII. SEQ ID NO:8 and SEQ ID NO:9 (MYb1 and MYb1.1) are B$_1$ external primers. SEQ ID NO:10 and SEQ ID NO:11 (MYb2 and MYb2.1) are B$_2$ external primers. B$_1$ and B$_2$ primers consist of target binding sequences and hybridize to the target upstream of S$_1$ and S$_2$ (FIG. 2). Extension of the B$_1$ and B$_2$ primers serves to displace the extension products of the S$_1$ and S$_2$ primers in the first cycle of SDA target generation. SEQ ID NO:12 (MYd1) is the detector probe used for specific detection of amplification products by primer extension analysis. Oligonucleotides SEQ ID NOS:4–12, were synthesized and gel purified by Synthetic Genetics (San Diego, Calif.).

The additional sequence information obtained from strains TMC1201, LCDC724 and 13638 showed a 3' mismatch of primer SEQ ID NO:4 (MYs1) with LCDC724. There were also several mismatches with LCDC 724 and TMC 1201 within SEQ ID NO:8 (MYb1), but no mismatches with p6123, p6232 or 13638. Therefore, the SEQ ID NO:9 (MYb1.1) B$_1$ primer was designed and synthesized as a perfect match with LCDC 724 and TMC 1201. The target regions of SEQ ID NO:5 and SEQ ID NO:6 were identical among all the strains sequenced. However, there were mismatches found in the target binding region of the detector probe, SEQ ID NO:12. As the detector probe is a 16met which is extended by a polymerase under low stringency conditions, these mismatches are unlikely to affect the detection of the amplification products.

The first set of SDA primers (SEQ ID NO:4, SEQ ID NO:6, SEQ ID NO:8 and SEQ ID NO:10) was designed based on the alignment of p6123 and p6232 only, as no sequence information for the additional strains was available at that time. This primer set detected the additional 3 isolates of *M. kansasii* tested (LCDC 724, 13638 and TMC 1201) and did not show any cross reactivity to *M. gastri*, *M. tuberculosis* or *M. avium*. However, the degree of amplification (the amplification factors) varied among the different isolates. Amplification was greatly reduced in LCDC724, possibly because of a 3' mismatch in the SEQ ID NO:4 primer (see below).

In an attempt to identify amplification primers for SDA which gave more consistent amplification factors, new S$_1$ and S$_2$ SDA primers were designed based on sequence alignments of all five *M. kansasii* strains. These were SEQ ID NO:5 and SEQ ID NO:7 (MYs1.1 and MYs2.1). Also, a new B$_2$ primer, SEQ ID NO:11 (MYb2.1), was designed and synthesized. SEQ ID NO:11 was identical to SEQ ID NO:10 (MYb2) except that the 5' nucleotide was an A instead of a G to make a perfect match to the p6123 sequence, which differs from p6232, TMC 1201, LCDC 724 and 13638. Different primer combinations were then tested to determine whether any gave consistent amplification factors in TMC 1201, LCDC 724 and 13638. The four combinations of amplification primers tested were as follows:

A) SEQ ID NO:4 and SEQ ID NO:6
  B) SEQ ID NO:4 and SEQ ID NO:7
  C) SEQ ID NO:5 and SEQ ID NO:6
  D) SEQ ID NO:5 and SEQ ID NO:7

Set A and Set C produced easily detectable levels of amplified target sequence in all three isolates. Set D amplified TMC 1201 and 13638 but performed poorly with LCDC 724. Set B produced no detectable amplification products in LCDC 724 but amplified well in TMC 1201 and 13638. These results were similar using any combination of bumper primers, as long as SEQ ID NO:11 was not included, as discussed below. The combination of SEQ ID NO:5, SEQ ID NO:6, SEQ ID NO:8 and SEQ ID NO:10 gave the best results with the most consistant amplification factors.

These results illustrate the unpredictable interactions between SDA primers—SEQ ID NO:4 contains a mismatch at the 3' end with LCDC 724. It is generally believed that the 3' end of the primer must be hybridized in order for polymerase to extend it efficiently. This is consistent with the lack of amplification when SEQ ID NO:4 is paired with SEQ ID NO:7. However, pairing the SEQ ID NO:4 amplification primer with SEQ ID NO:6 unexpectedly allows efficient amplification in all three isolates in spite of the 3' mismatch. Both SEQ ID NO:7 and SEQ ID NO:6 are perfect matches for the target sequence and would be expected to have little effect on amplification when paired with the same opposite amplification primer. The selection of the bumper primers also had unpredictable and unexpected effects on amplification. SEQ ID NO:10 contains a mismatch at the 5' end. SEQ ID NO:11 was designed to correct the mismatch and create a perfectly matched bumper primer. However, rather than improving amplification, SEQ ID NO:11 unexpectedly depressed it to almost undetectable levels. In contrast, the bumper primer containing the 5' mismatch functioned normally and allowed normal levels of amplification.

To compensate for the effects of primer mismatches, unconventional SDA primer sets were assembled. Whereas SDA has previously been performed only with two amplification primers and two bumper primers, these unconventional primer sets contained additional amplification and bumper primers which could potentially hybridize more efficiently to the variable sequences. For example, SDA using SEQ ID NO:4, SEQ ID NO:5, and SEQ ID NO:6 (three amplification primers) with SEQ ID NO:8, SEQ ID NO:10 and SEQ ID NO:11 (three bumper primers) provided species-specific amplification at a slightly reduced level, but had the advantage of essentially eliminating the variability in amplification factors among the isolates. This was unexpected, as SEQ ID NO:11 almost eliminated amplification when used in conventional primer pairs (see above). The severely inhibitory effect of SEQ ID NO:11 appeared to be overcome when three amplification primers and three bumper primers were used. SDA using SEQ ID NO:5 and SEQ ID NO:6 (two amplification primers) with SEQ ID NO:8, SEQ ID NO:9, and SEQ ID NO:10 (three bumper primers) allowed amplification in the strains which were not amplified using SEQ ID NO:8 alone as the $B_1$ primer and also improved the consistency of amplification factors among the various isolates.

To further demonstrate the species-specific amplification using the primers, DNA from 74 isolates of *M. kansasii* were tested by SDA using SEQ ID NO:5, SEQ ID NO:6, SEQ ID NO:8, SEQ ID NO:9, and SEQ ID NO:10. These included 17 isolates from Australia (14 clinical and 3 environmental), two clinical isolates from the Solomon Islands, 11 clinical isolates from Japan, five isolates from England (one clinical and four respiratory), 11 clinical isolates from the United States, four clinical isolates from South Africa, 11 isolates from Switzerland (nine urine, 1 clinical and 1 sputum), four isolates from Belgium (3 clinical and 1 urine). Five laboratory strains (LCDC 711, LCDC 714, LCDC 715, LCDC 725 and D-31) were tested in addition to TMC 1201, 13638 and LCDC 724. A specific amplification product was detected by hybridization and polymerase extension of the $^{32}$P-labeled primer (SEQ ID NO:12) in all of these DNA samples. This SDA system did not cross react with any of the other Mycobacteria tested, i.e., there were no detectable amplification products produced in *M. gastri, M. avium, M. tuberculosis, M. bovis, M. chelonae, M. fiavescens, M. fortuitum, M. gordonae, M. intracelhdare, M. marinun, M. microti, M. malmoense, M. smegmatis, M. szulgai* or *M. xenopi*. In addition, this set of primers does not cross react with *Nocardia asteroides* or *Rhodococcus rhodochrous*, which are closely related to mycobacteria.

The foregoing experimental examples are given as illustrations of certain embodiments of the invention and are not to be construed as limiting the invention defined by the appended claims.

What is claimed is:

1. A set of primers for species-specific amplification of *Mycobacterium kansasii* target nucleic acids comprising a first amplification primer consisting of nucleotides 26–38 of SEQ ID NO:5 and a second amplification primer consisting of nucleotides 25–37 of SEQ ID NO:6.

2. A set of primers for species-specific amplification of *Mycobacterium kansasii* target nucleic acids comprising a first amplification primer consisting of SEQ ID NO:5 and a second amplification primer consisting of SEQ ID NO:6.

3. The set of primers of claim 2 further comprising a first bumper primer consisting of SEQ ID NO:8 and a second bumper primer consisting of SEQ ID NO:10.

4. The set of primers of claim 3 further comprising a third bumper primer consisting of SEQ ID NO:9.

5. A set of primers for species-specific amplification of *Mycobacterium kansasii* target nucleic acids comprising a first amplification primer consisting of nucleotides 25–37 of SEQ ID NO:4 and a second amplification primer consisting of nucleotides 25–37 of SEQ ID NO:6.

6. The set of primers of claim 5 further comprising a first bumper primer consisting of SEQ ID NO:8 and a second bumper primer consisting of SEQ ID NO:10.

7. The set of primers of claim 6 further comprising a third bumper primer consisting of SEQ ID NO:11.

8. The set of primers of claim 7 further comprising a third amplification primer consisting of SEQ ID NO:5.

9. A method for species-specific detection of a double stranded *Mycobacterium kansasii* nucleic acid target sequence comprising:

a) hybridizing to the *Mycobacterium kansasii* nucleic acid target sequence, if present, a first amplification primer consisting of nucleotides 26–38 of SEQ ID NO:5 and a second amplification primer consisting of nucleotides 25–37 of SEQ ID NO:6;

b) amplifying the *Mycobacterium kansasii* nucleic acid target sequence by extending the hybridized first and second amplification primers with polymerase to produce extension products and displacing the extension products, and;

c) detecting the amplified *Mycobacterium kansasii* nucleic acid target sequence.

10. A method for species-specific detection of a double stranded *Mycobacterium kansasii* nucleic acid target sequence comprising:

a) hybridizing to the *Mycobacterium kansasii* nucleic acid target sequence, if present, a first amplification primer comprising a first target binding sequence consisting of nucleotides 26–38 of SEQ ID NO:5 and a second amplification primer comprising a second target binding sequence consisting of nucleotides 25–37 of SEQ ID NO:6, the first and second amplification primers further comprising a restriction endonuclease recognition site 5' to the first and second target binding sequences;

b) generating a target fragment containing the *Mycobacterium kansasii* nucleic acid target sequence by extending the hybridized first and second amplification primers to produce first and second extension products, and displacing the first and second extension products;

c) amplifying the *Mycobacterium kansasii* nucleic acid target sequence by nicking the restriction endonuclease recognition site in the target fragment, extending from the nick using exonuclease deficient polymerase, and displacing copies of the target sequence, and;

d) detecting the amplified *Mycobacterium kansaii* nucleic acid target sequence.

11. The method of claim 10 wherein the first amplification primer consists of SEQ ID NO:5 and the second amplification primer consists of SEQ ID NO:6.

12. The method of claim 11 wherein the first and second extension products are displaced by extension of a first bumper primer consisting of SEQ ID NO:8 and a second bumper primer consisting of SEQ ID NO:10.

13. The method of claim 12 further comprising hybridization and extension of a third bumper primer consisting of SEQ ID NO:9.

14. A method for species-specific detection of a double stranded *Mycobacterium kansasii* nucleic acid target sequence comprising:

a) hybridizing to the *Mycobacterium kansaii* nucleic acid target sequence, if present, a first amplification primer consisting of nucleotides 25–37 of SEQ ID NO:4 and a second amplification primer consisting of nucleotides 25–37 of SEQ ID NO:6;

b) amplifying the *Mycobacterium kansaii* nucleic acid target sequence by extending the hybridized first and second amplification primers with polymerase to produce extension products and displacing the extension products, and;

c) detecting the amplified *Mycobacterium kansaii* nucleic acid target sequence.

15. A method for species-specific detection of a double stranded *Mycobacterium kansasii* nucleic acid target sequence comprising:

a) hybridizing to the *Mycobacterium kansaii* nucleic acid target sequence, if present, a first amplification primer comprising a first target binding sequence consisting of nucleotides 25–37 of SEQ ID NO:4 and a second amplification primer comprising a second target binding sequence consisting of nucleotides 25–37 of SEQ ID NO:6, the first and second amplification primers further comprising a restriction endonuclease recognition site 5' to the first and second target binding sequences;

b) generating a target fragment containing the *Mycobacterium kansaii* nucleic acid target sequence by extending the hybridized first and second amplification primers to produce first and second extension products, and displacing the first and second extension products;

c) amplifying the *Mycobacterium kansaii* nucleic acid target sequence by nicking the restriction endonuclease recognition site in the target fragment, extending from the nick using exonuclease deficient polymerase, and displacing copies of the target sequence, and;

d) detecting the amplified *Mycobacterium kansaii* nucleic acid target sequence.

16. The method of claim 15 wherein the first amplification primer consists of SEQ ID NO:4 and the second amplification primer consists of SEQ ID NO:6.

17. The method of claim 16 wherein the first and second extension products are displaced by extension of a first bumper primer consisting of SEQ ID NO:8 and a second bumper primer consisting of SEQ ID NO:10.

18. The method of claim 17 further comprising hybridization and extension of a third bumper primer consisting of SEQ ID NO:11.

19. The method of claim 18 further comprising hybridization of a third amplification primer consisting of SEQ ID NO:5.

\* \* \* \* \*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:1:

TGAAACGTGT TTTGCCAGCG                                          20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:2:

ACCAGCGGAT CGTCACGGTG                                          20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:3:

ACCAGCGGGT CGTCACGGTG                                                               20

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19..24
        ( D ) OTHER INFORMATION: /function="HincII recognition
            site"

( i x ) FEATURE:
        ( A ) NAME/KEY: misc_binding
        ( B ) LOCATION: 25..37
        ( D ) OTHER INFORMATION: /function="hybridization to target
            sequence"
            / standard_name="target binding sequence"

( x i ) SEQUENCE DESCRIPTION: SEQ ID NO:4:

TTGAATAGTC GGTTACTTGT TGACCAGCAC CTCGGCG                                             37

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19..24
        ( D ) OTHER INFORMATION: /function="HincII recognition
            site"

( i x ) FEATURE:
        ( A ) NAME/KEY: misc_binding
        ( B ) LOCATION: 26..38
        ( D ) OTHER INFORMATION: /function="hybridization to target
            sequence"
            / standard_name="target binding sequence"

( x i ) SEQUENCE DESCRIPTION: SEQ ID NO:5:

TTGAATAGTC GGTTACTTGT TGACAGAACA GCACCTCG                                            38

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19..24
        ( D ) OTHER INFORMATION: /function="HincII recognition
            site"

( i x ) FEATURE:
        ( A ) NAME/KEY: misc_binding
        ( B ) LOCATION: 25..37
        ( D ) OTHER INFORMATION: /function="hybridization to target sequence"
/ standard_name="target binding sequence"

( x i ) SEQUENCE DESCRIPTION: SEQ ID NO:6:

TTGAAGTAAC CGACTATTGT TGACCGATTC CTGGTGG 37

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19..24
        ( D ) OTHER INFORMATION: /function="HincII recognition
            site"

( i x ) FEATURE:
        ( A ) NAME/KEY: misc_binding
        ( B ) LOCATION: 25..37
        ( D ) OTHER INFORMATION: /function="hybridization to target
            sequence"
        / standard_name="target binding sequence"

( x i ) SEQUENCE DESCRIPTION: SEQ ID NO:7:

TTGAAGTAAC CGACTATTGT TGACAGCGTT CTGCGAC 37

( 2 ) INFORMATION FOR SEQ ID NO:8:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCGGCCAACA G 11

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ACGGTGCTGC GGC 13

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GTCGGTGTGG CA 12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATCGGTGTGG CA                                                          12
```

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
AACTCGACGG CCTCGG                                                      16
```

( 2 ) INFORMATION FOR SEQ ID NO:13:

( i ) SEQUENCE CHARACTERISTICS:
        ( A ) LENGTH: 200 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:13:

```
ACCAGCGGAT CGTCACGGTG CTGCGGCCAG ACGACGGTAC GGCCGGCCAG CAGCGCCACG        60
GTGGGGTACC CGTCGAACAG CACCTCGGCG AACTCGACCG CCTCGGGCGC CCACCAGGAA       120
TCGTCGTCGC AGAACGCGAC AAACGGTGTG TCGCAGTATG CCACACCGAT GTTGCGAGCC       180
ACCGCGCCCT GGTTGCGGGT                                                  200
```

( 2 ) INFORMATION FOR SEQ ID NO:14:

( i ) SEQUENCE CHARACTERISTICS:
        ( A ) LENGTH: 200 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:14:

```
ACCAGCGGGT CGTCACGGTG CTGCGGCCAG ACGACGGTTC GGCCTGCCAG TAGCGCCACG        60
GTGGGATACG CGTCGAACAG CACCTCGGCA AACTCGACGG CCCCGGGCGC CCACCAGGAA       120
TCGTCGTCGC AGAACGCGAC AAAAGGTGTG CTGCATTGTG CCACACCGAT ATTGCGGGCT       180
ACGGCGCCTT GGTTGCGGGT                                                  200
```

( 2 ) INFORMATION FOR SEQ ID NO:15:

( i ) SEQUENCE CHARACTERISTICS:
    ( A ) LENGTH: 200 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Mycobacterium kansasii ( x i ) SEQUENCE DESCRIPTION: SEQ ID NO:15:

| | | | | | | |
|---|---|---|---|---|---|---|
| ACCAGCGGGT | CGTCACGGTG | TTGCGGCCAC | ACGACGGTAC | GGCCGGCCAA | CAGGGCCACG | 60 |
| GTGGGATACG | CGTCGAACAG | CACCTCGGCG | AACTCGACGG | CCTCGGGTGC | CCACCAGGAA | 120 |
| TCGTCGTCGC | AGAACGCGAC | AAACGGTGTG | CCGCATACTG | CCACACCGAT | GTTGCGGGCC | 180 |
| ACCGCGCCCT | CGTTGCGGGT | | | | | 200 |

( 2 ) INFORMATION FOR SEQ ID NO:16:

( i ) SEQUENCE CHARACTERISTICS:
    ( A ) LENGTH: 171 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:16:

| | | | | | | |
|---|---|---|---|---|---|---|
| ACCAGCGGAT | CGTCACGGTG | CTGCGGCCAG | ACGACAGTAC | GGCCGGCCAA | CAGCGCGACG | 60 |
| CTGGGATATC | CGTCGAACAG | CACCTCGGCG | AACTCGACGG | CCTCGGGCGC | CCACCAGGAA | 120 |
| TCGCCGTCGC | AGAACGCGAC | AAACGGTGTG | TCGCAATGTG | CCACACCGAC | G | 171 |